(12) United States Patent
Kose

(10) Patent No.: US 7,625,620 B2
(45) Date of Patent: Dec. 1, 2009

(54) SHEET-TYPE PATCH

(75) Inventor: Yasuhisa Kose, Saga (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 10/508,142

(22) PCT Filed: Mar. 12, 2003

(86) PCT No.: PCT/JP03/02916

§ 371 (c)(1),
(2), (4) Date: Sep. 17, 2004

(87) PCT Pub. No.: WO03/082164

PCT Pub. Date: Oct. 9, 2003

(65) Prior Publication Data

US 2005/0181163 A1     Aug. 18, 2005

(30) Foreign Application Priority Data

Mar. 28, 2002 (JP) .............................. 2002-091297

(51) Int. Cl.
*B32B 9/00* (2006.01)
*B65D 65/28* (2006.01)
*B32B 3/10* (2006.01)

(52) U.S. Cl. ...................... 428/40.1; 428/42.2; 428/43; 428/131; 428/137; 428/138

(58) Field of Classification Search ................ 428/40.1, 428/41.5, 41.7, 41.8, 42.2, 42.3, 43, 343, 428/131, 137, 138, 204.4; 424/443
See application file for complete search history.

(56) References Cited

U.S. PATENT DOCUMENTS

| 4,545,372 | A | * | 10/1985 | Lauritzen ..................... 206/441 |
| 4,562,102 | A | * | 12/1985 | Rabuse et al. ................. 428/43 |
| 4,772,499 | A | * | 9/1988 | Greenway ..................... 428/43 |
| 6,238,762 | B1 | * | 5/2001 | Friedland et al. .............. 428/43 |
| 6,368,689 | B1 | * | 4/2002 | Connor Sledge et al. ...... 428/43 |
| 2003/0138479 | A1 | * | 7/2003 | Mizota et al. ............... 424/443 |

FOREIGN PATENT DOCUMENTS

| JP | 60-10434 | 7/1985 |
| JP | 2000-166965 | 6/2000 |

* cited by examiner

*Primary Examiner*—Patricia L Nordmeyer
(74) *Attorney, Agent, or Firm*—Peter F. Corless; Colleen J. McKiernan; Edwards Angell Palmer & Dodge LLP

(57) ABSTRACT

It is intended to provide a sheet-type patch which is safe to the skin, imparts a good feel in using, shows an excellent function as well as a cooling effect on the affected part, can be easily torn by hand into a desired size even in the state of a preparation provided with a release film bonded thereto, and can be stably used or stored after tearing. Namely, a sheet-type patch composed of a support made from yarns of 1 to 80 mm in fiber length, an ointment base and a release film having been punched so as to give pores of 10 to 1200 μm in size.

13 Claims, No Drawings

SHEET-TYPE PATCH

TECHNICAL FIELD

The present invention relates to a sheet-type patch. More particularly, the present invention relates to a sheet-type patch for a cosmetic, medicinal, or quasi-drug preparation, which is a patch for compress used for the body, low back, arm, leg, face or the like, and can be easily torn by hand into a necessary size in the state of the preparation provided with a release film attached thereto, and the remaining part can be stably used or stored.

BACKGROUND ART

Sheet-type patches that are used as tape preparations and wet compresses for the treatment of backache, shoulder stiffness, bruising, sprains or the like, wet compresses for healing foot tiredness, sheet-form pack preparations for beauty treatments for the face or body, etc. are known. For example, an aqueous adhesive composition that is composed of a polyacrylic acid, a polyacrylate salt, a cellulose derivative, a polyhydric alcohol and a polyvalent metal compound is disclosed in JP-B-3-16989, a cataplasm preparation which does not contain any medicinal components and which is formed by blending a moisturizing component selected from sodium hyaluronate, sodium chondroitin sulfate, a lactate salt, a pyrrolidone carboxylic acid, urea, aloe extract and *perilla* leaf extract is disclosed in JP-A-8-291057, and a foot care sheet preparation for the purpose of eliminating tiredness and swelling of feet or the like that has an improved effect of providing a refreshing feeling or the like due to a component in a hydrated adhesive layer and excellent usability is disclosed in JP-A-10-279473. Meanwhile, an adhesive tape easily torn by hand is disclosed in JP-B-50-13306, JP-A-3-47885 and JP-A-9-324155, and an adhesive tape easily torn by hand, to which a laminated film and an acrylic adhesive, a rubber adhesive, a polyolefin adhesive or the like is applied, is disclosed in JP-A-2002-36406.

However, among the conventional sheet-type patches having a tearable property disclosed in the above documents or the like, there are few examples introduced as a state of the preparation provided with a release film attached thereto. Furthermore, they have the problems that they cannot be easily torn by hand, they cannot torn at a desired position, whereby the size is not appropriate, the external appearance is not preferable when they are torn by hand because of a break or a snag at the torn surface, and the remaining part cannot be stably used or stored. Some disclose a cutting method by providing, at regular intervals, perforated lines or the like penetrating a support, a paste and a release film. However, it cannot satisfy users' needs at all of using it by easily tearing by hand into a necessary size for a necessary affected part when needed without wasting it.

DISCLOSURE OF THE INVENTION

To solve the above-mentioned conventional problems, the present invention makes it an object to provide a sheet-type patch, which is safe for the skin, imparts a good feeling of use, shows an excellent acting effect as well as a cooling effect on the affected part, and further can be used by easily tearing it by hand into a necessary size in the state of the preparation provided with a release film attached thereto and the remaining part can be stably used or stored.

BEST MODE FOR CARRYING OUT THE INVENTION

In order to attain the above-mentioned object, the sheet-type patch of the present invention is composed of the following configuration.

"A sheet-type patch composed of a support made from a yarn of 1 to 80 mm in fiber length, a paste and a release film having been punched to have a hole on it of 10 to 1200 μm in diameter."

A release film used for the sheet-type patch of the present invention is characterized in that it is a film having been punched to have a hole on it of 10 to 1200 μm in diameter, however, the hole diameter is, more preferably, 20 to 500 μm. When the hole diameter is 20 μm or less, a tendency that deterioration of a hand-tearable property due to an increase in breaking strength of the film is occurred, or a break or a snag at the torn surface are likely to occur is observed, and in particular, in the case of less than 10 μm, the tendency is significant, therefore, it is not preferable. When the hole diameter is 500 μm or more, a tendency that shape degradation such as a break due to a decrease in breaking strength is occurred, or a decrease in workability or line qualification on production or a decrease in stability due to exudation or volatilization and evaporation is occurred is observed, and in particular, in the case of exceeding 1200 μm, the tendency is significant, therefore, it is not preferable.

The release film used for the sheet-type patch of the present invention is preferably a film having been punched in both longitudinal and lateral rows.

Also, the distance between the centers of the longitudinally and laterally adjoining holes is preferably 100 to 2000 μm, and more preferably the distance between the centers of the longitudinally and laterally adjoining holes is 500 to 1500 μm. When the distance between the centers of the longitudinally and laterally adjoining holes is 500 μm or less, a tendency that shape degradation such as a break due to a decrease in breaking strength is occurred, or a decrease in workability or line qualification on production or a decrease in stability due to volatilization and evaporation is occurred is observed, and in particular, in the case of less than 100 μm, the tendency is significant, therefore, it is not preferable. When the distance between the centers of the longitudinally and laterally adjoining holes is 1500 μm or more, a tendency that deterioration of the hand-tearable property due to an increase in breaking strength of the film is occurred or a break or a snag at the torn surface are likely to occur is observed, and in particular, in the case of exceeding 2000 μm, the tendency is significant, therefore, it is not preferable. In other words, by the balance of the diameter of the processed holes and the distance between the centers of the longitudinally and laterally adjoining holes, the hand-tearable property is significantly improved.

With regard to the release film used for the sheet-type patch of the present invention, the thickness of the film is preferably 20 to 150 μm, and more preferably the thickness is 40 to 120 μm. When the thickness is 40 μm or less, a tendency that shape degradation such as a break due to a decrease in breaking strength is occurred, or a decrease in workability or line qualification on production is occurred is observed, and in particular, in the case of less than 20 μm, the tendency is significant, therefore, it is not preferable. When the thickness is 120 μm or more, a tendency that deterioration of the hand-tearable property due to an increase in breaking strength of the film is occurred or a break or a snag at the torn surface are likely to occur is observed, and in particular, in the case of exceeding 150 μm, the tendency is significant, therefore, it is not preferable.

With regard to the release film used for the sheet-type patch of the present invention, the maximum strength of the tensile strength is preferably 10 to 100 N/50 mm, and more preferably the maximum strength of the tensile strength is 15 to 65 N/50 mm. When the maximum strength of the tensile strength is 15 N/50 mm or less, a tendency that shape degradation such as a break due to a decrease in breaking strength is occurred, or a decrease in workability or line qualification on production is occurred is observed, and in particular, in the case of less than 10 N/50 mm, the tendency is significant, therefore, it is not preferable. When the maximum strength of the tensile strength is 65 N/50 mm or more, a tendency that deterioration of the hand-tearable property due to an increase in breaking strength of the film is occurred or a break or a snag at the torn surface are likely to occur is observed, and in particular, in the case of exceeding 100 N/50 mm, the tendency is significant, therefore, it is not preferable. Incidentally, the tensile strength of the punched release film was measured in accordance with the method described in JIS L1912 "tensile strength and elongation rate" in "Iryouyou Fusyokufu Shiken Houhou (Test method for unwoven fabrics for medical use)", and is shown by the value of the measurement under the conditions that the sample width was 50 mm, the distance between clamps was 50 mm and the tensile speed was 300 mm/min.

Examples of a material of the release film used for the sheet-type patch of the present invention include materials such as polyethylene, polypropylene, polyethylene terephthalate, an ethylene vinyl acetate copolymer, an ethylene vinyl alcohol copolymer, polyvinyl chloride, polyurethane, polyester, polyamide, and a film formed by combining one or more materials selected from the above can be used as a material of the release film used for the sheet-type patch of the present invention.

These release films used for the sheet-type patch of the present invention can be appropriately processed to have on them dashed lines, perforated lines, prints or can be subjected to a releasability treatment or the like for the purpose of improving the releasability and adhesive property, or can be embossed or the like for the purpose of improving the external appearance and preventing sliding.

With regard to a support used for the sheet-type patch of the present invention, the maximum strength of the tensile strength is preferably 3 to 50 N/50 mm, and more preferably 5 to 40 N/50 mm. When the maximum strength of the tensile strength of the support is 5 N/50 mm or less, a tendency that shape degradation such as a break is occurred is observed, and in particular, in the case of less than 3 N/50 mm, the tendency is significant, therefore, it is not preferable. When the maximum strength of the tensile strength of the support is 40 N/50 mm or more, a tendency that deterioration of the hand-tearable property is occurred or deterioration of feeling of use (pressing feeling or the like) due to poor elongation of the support is occurred is observed, and in particular, in the case of exceeding 50 N/50 mm, the tendency is significant, therefore, it is not preferable.

At this time, the elongation at maximum load of the support relative to the initial length is preferably 3 to 100%, and more preferably 3 to 50%. When the elongation at maximum load of the support is less than 3%, the tendency that shape degradation such as a break or deterioration of feeling of use (pressing feeling or the like) is occurred is significant, therefore it is not preferable. When the elongation at maximum load of the support is 50% or more, a tendency that shape degradation such as a sag or a wrinkle or deterioration of the hand-tearable property is occurred is observed, and in particular, in the case of exceeding 100%, the tendency is significant, therefore, it is not preferable. Incidentally, the tensile strength and the elongation at maximum load of the support were measured in accordance with the method described in JIS L1912 "tensile strength and elongation rate" in "Iryouyou Fusyokufu Shiken Houhou (Test method for unwoven fabrics for medical use)", and are shown by the values of the measurement under the conditions that the sample width was 50 mm, the distance between clamps was 50 mm and the tensile speed was 300 mm/min.

Furthermore, the weight per unit area of the support is preferably 20 to 200 g/m$^2$ and more preferably 40 to 120 g/m$^2$. When the weight per unit area of the support is 40 g/m$^2$ or less, a tendency that shape degradation such as a break, or poor appearance or poor forming due to exudation on applying the paste is occurred is observed, and in particular, in the case of less than 20 g/m$^2$, the tendency is significant, therefore, it is not preferable. When the weight per unit area of the support is 120 g/m$^2$ or more, a tendency that deterioration of feeling of use or deterioration of the hand-tearable property due to poor elongation or poor flexibility of the support is occurred, and furthermore, an increase in cost is caused is observed, and in particular, in the case of exceeding 200 g/m$^2$, the tendency is significant, therefore, it is not preferable.

Still further, as for the color of the support, it is not particularly limited, however, it greatly affects the image of the preparation and leads to improvement of feeling of use and activation feeling to the skin. Examples of the color include white, skin color, yellow, red, orange, green, blue, pink, light blue, brown and the like, and if necessary a shade is preferably adjusted. Also, printing process, embossing process or the like can be carried out as needed.

Examples of a material of the support used for the sheet-type patch of the present invention include materials such as polyethylene, polypropylene, polyethylene terephthalate, an ethylene vinyl acetate copolymer, polyvinyl chloride, polyurethane, polyester, polyamide, rayon, pulp, cotton, and a nonwoven fabric made by entangling, heat fusion bonding, pressure bonding or binder bonding in combination with one or more materials selected from the above can be used as a material of the support for the sheet-type patch of the present invention.

The fiber length of a yarn used as a material at this time is generally 1 to 80 mm, more preferably 10 to 50 mm. When the fiber length is 10 mm or less, a tendency that shape degradation such as a break due to a decrease in breaking strength of the support is occurred, or a decrease in workability or line qualification on production is occurred is observed, and in particular, in the case of less than 1 mm, the tendency is significant, therefore, it is not preferable. When the fiber length is 50 mm or more, a tendency that deterioration of the hand-tearable property due to an increase in breaking strength of the support is occurred or a snag at the torn surface are likely to occur is observed, and in particular, in the case of exceeding 80 mm, the tendency is significant, therefore, it is not preferable. In particular, in the case of making a nonwoven fabric by heat fusion bonding of short fibers as the production method of a nonwoven fabric, the hand-tearable property is significantly improved.

The sheet-type patch of the present invention retains the stability of the preparation by applying a paste to the support according to the present invention, and further covering the surface of the paste layer with the release film according to the present invention.

In the sheet-type patch of the present invention, examples of a base of the paste applied to the support include, for example, a moisturizing agent, water, a water-soluble polymer, a crosslinking agent, an antiseptic and the like. In addition, a medicinal component, a skin-beautifying component, a moisturizing component, an antioxidant, a tackifier, a solubilizer, a pigment, a fragrance, a surfactant, a UV absorber, an inorganic filler, a pH adjusting agent and the like can be blended as needed.

With regard to the moisturizing agent, a glycol and/or a polyhydric alcohol can be used singly or by combining both. The blended amount of the moisturizing agent relative to the total amount of the base is 1 to 50 wt %, preferably 5 to 30 wt %, and more preferably 5 to 25 wt %. When the blended amount is 5 wt % or less, a tendency that lowering of the adhesive property or agglutinating property of the preparation, lowering of the water holding property or shape retaining property before use, non-uniformization of gel, a decrease in workability or deterioration of feeling of use during use is occurred is observed, and in the case of less than 1 wt %, the tendency is significant, therefore, it is not preferable. When the blended amount is 25 wt % or more, the adhesive property or agglutinating property of the preparation, the water holding property or shape retaining property before use is lowered, and a tendency that a decrease in workability or deterioration of feeling of use during use is occurred is observed, and in particular, in the case of exceeding 50 wt %, the tendency is significant, therefore, it is not preferable.

In addition, the glycol that is a moisturizing agent can be used as a dispersant/solubilizer or a plasticizer for a water-soluble polymer, a moisturizing component, a crosslinking agent, a skin-beautifying component, an antiseptic or the like, and can also be used to promote a releasability and diffusion property of water. Since the glycols referred to here have a polyether structure and have poor hydrophilicity due to the presence of fewer hydroxyl groups compared with a polyhydric alcohol with low molecular weight that are commonly used, by utilizing this property, the critical relative humidity of the base components excluding water can be lowered, and a larger amount of water can be released to the outside when the product is used. As a result, the skin is moisturized, the heat of vaporization is removed by volatilizing water to the outside, flushing of the face and inflammation can be suppressed while a comfortable refreshing feeling is given. Furthermore, the temperature dependence of the viscosity is low, and when the glycols are blended in a preparation, a stable shape retaining property which is independent from the changes in the surroundings can be exhibited. With regard to the glycols having a polyether structure, polyethylene glycol with an average molecular weight of 200 to 600 and polypropylene glycol with an average molecular weight of 500 to 3000 are preferable, and they can be used by blending one or more kinds of these.

The polyhydric alcohol that is a moisturizing agent can be used as a dispersant/solubilizer or a plasticizer for a water-soluble polymer, a moisturizing component, a crosslinking agent, a skin-beautifying component, an antiseptic or the like, and can also suppress the releasability and diffusion property of water. The polyhydric alcohols referred to here are polyhydric alcohols with low molecular weight having 2 to 3 hydroxyl groups in the each molecule, and since they have excellent hydrophilicity, the critical relative humidity of the base components excluding water can be improved and the release and diffusion of water during use can be suppressed. With regard to the polyhydric alcohol, propylene glycol, 1,3-butylene glycol and glycerin are preferable, and they can be used by blending one or more of them. By the blending balance of the glycols and/or polyhydric alcohols with water in these moisturizing agents, an appropriate moisturizing property and adhesive property are given to the skin and not only a comfortable refreshing feeling during attachment, but also a satisfying feeling of use after detachment is significantly improved.

As the water, purified water, sterile water and natural water can be used. Water acts as a dispersant/solubilizer for a water-soluble polymer, a moisturizing component, a crosslinking agent, an antiseptic and the like, and is especially important to disperse and dissolve a glycol or a polyhydric alcohol, which is a moisturizing agent, uniformly in the preparation. Further, water itself significantly increases feeling of use both during use and after use, and penetrates into the skin together with a moisturizing component, bringing an effect to give moisture and tension. From these viewpoints, the water needs to be added in a large amount such as, the blended amount is 30 to 95 wt %, preferably 65 to 90 wt %, more preferably 70 to 85 wt %. By allowing a large amount of water to be included in the preparation, the relative humidity of the preparation itself can be heightened, and it becomes possible to effectively drain off a large amount of water to the outside during use, and consequently giving moisture to the skin and removing the heat of vaporization by evaporation of water to the outside, whereby it is possible to impart a comfortable refreshing feeling. When the blended amount of water is 70 wt % or less, there is a tendency that lowering of the adhesive property of the preparation or the water holding property before use, a decrease in workability or deterioration of feeling of use during use is caused, and in the case of less than 30 wt %, the tendency is significant, therefore, it is not preferable. When the blended amount is 85 wt % or more, the adhesive property or agglutinating property is likely to be inhibited, and there is a tendency that the shape retaining property before use is lowered, and in the case of exceeding 95 wt %, the tendency is significant, therefore, it is not preferable.

Examples of the water-soluble polymer include gelatin, polyacrylic acid, the salt thereof, partial neutralization product thereof and the like, and each can be used singly or by blending two or more of them. As a salt of the polyacrylic acid salts, salts of metals such as sodium, lithium and potassium are preferable, and the one whose average degree of polymerization is 1000 to 100000 is preferably used. As a blended amount of these water-soluble polymers, it is used at 3 to 25 wt %, preferably 5 to 20 wt %, and more preferably 5 to 10 wt %. When the blended amount is 5 wt % or less, the adhesive property, agglutinating property, shape retaining property, water absorption ability or the like of the preparation is lowered, and a tendency of causing non-uniformization of the paste or a decrease in workability or deterioration of feeling of use is likely to be caused, and in the case of less than 3 wt %, the tendency is significant, therefore, it is not preferable. When the blended amount is 10 wt % or more, a tendency of causing non-uniformization of paste or a decrease in workability or deterioration of feeling of use is likely to be caused as well as deteriorating the adhesive property, agglutinating property or shape retaining property of the preparation and excessively increasing the viscosity during production process, and in the case of exceeding 25 wt %, the tendency is significant, therefore, it is not preferable.

As the crosslinking agent, a water-insoluble aluminum compound or a polyfunctional epoxy compound can be used singly or by blending two or more of them. Examples of the water-insoluble aluminum compound include aluminum hydroxide, aluminum hydroxide gel, aluminum silicate hydrate, synthetic aluminum silicate, kaolin, aluminum acetate, aluminum lactate, aluminum stearate, magnesium metasilicate aluminate, magnesium silicate aluminate and the like, and one or more kinds of these can be used by blending.

Use of the water-insoluble aluminum compound gives gel an appropriate strength in an initial physical property as a filler in addition to an inhibitory effect for skin irritation by the antacid action and a skin astringent action by a trace amount of aluminum ion, and along with this, aluminum ion dissolves into the preparation in a time course, thereby it is possible to show a function to cover the lowering of the gel strength owing to time dependent decomposition of polymer and time dependent cleavage of a crosslinking part of the covalent bond between polymers. Further, the aluminum dissolution rate can be controlled by adjusting the pH.

Examples of the polyfunctional epoxy compound include polyethyleneglycol diglycidyl ether, ethyleneglycol diglycidyl ether, glycerin diglycidyl ether, glycerin triglycidyl ether, propyleneglycol diglycidyl ether, polyglycerol polyglycidyl ether, sorbitol polyglycidyl ether, sorbitan polyglycidyl ether, trimethylolpropane polyglycidyl ether, pentaerythritol polyglycidyl ether, resorcinol diglycidyl ether, neopentylglycol diglycidyl ether and the like. One or more kinds of these polyfunctional epoxy compounds can be used by blending. An excellent water absorption ability and shape retaining property can be obtained by using the polyfunctional epoxy compound, and they can efficiently form a covalent bond with a water-soluble polymer having a carboxyl group, an amino group, a hydroxyl group or the like, and can enhance a gel strength.

As the blended amount of these crosslinking agents, it is used at 0.05 to 20 wt %, preferably 0.5 to 15 wt %, and more preferably 1 to 10 wt %. When the blended amount is 1 wt % or less, a tendency that lowering of the agglutinating property or shape retaining property of the preparation, lowering of the water absorption ability, lowering of time dependent stability in a physical property of the preparation, a decrease in workability, a decrease in safety for the skin or deterioration of feeling of use is occurred is observed, and in particular, in the case of less than 0.05 wt %, the tendency is significant, therefore, it is not preferable. When the blended amount is 10 wt % or more, a tendency that an increase in the adhesive property, agglutinating property, shape retaining property and excessive viscosity during production, non-uniformization of paste due to gelation, a decrease in workability, a decrease in safety for the skin or a deterioration of feeling of use is occurred is observed, and in particular, in the case of exceeding 20 wt %, the tendency is significant, therefore, it is not preferable.

Examples of the antiseptic include p-hydroxybenzoate ester (for example, methylparaben, ethylparaben, propylparaben), 1,2-pentanediol, benzoic acid, benzoate, salicylate, sorbic acid, sorbate, dehydroacetate, 4-isopropyl-3-methylphenol, 2-isopropyl-5-methylphenol, phenol, hinokitiol, cresol, 2,4,4'-trichloro-2'-hydroxydiphenyl ether, 3,4,4'-trichlorocarbanide, chlorobutanol, benzalkonium chloride, benzethonium chloride and the like, and one or more kinds of these can be used by blending. Among these, p-hydroxybenzoate ester is preferable. As the blended amount, it is used at 0.005 to 10 wt %, preferably 0.01 to 5 wt %, and more preferably 0.01 to 1 wt %. When the blended amount is 0.01 wt % or less, there is a tendency that putrefaction of the preparation due to an outbreak of fungi or bacteria during storage or lowering of feeling of use during use and after use is occurred, and in the case of less than 0.005 wt %, the tendency is significant, therefore, it is not preferable. When the blended amount is 1 wt % or more, there is a tendency that a subtle change in the adhesive property or agglutinating property in the preparation is occurred and an effect to give an uncomfortable feeling or the like due to irritation or odor of the antiseptic with respect to feeling of use is brought about, and in the case of exceeding 10 wt %, the tendency is significant, therefore, it is not preferable.

In the paste used for the sheet-type patch of the present invention, in addition to the above-mentioned base components, a medicinal component, a skin-beautifying component, a moisturizing component, an antioxidant, a tackifier, a solubilizer, a pigment, a fragrance, a surfactant, a UV absorber, an inorganic filler, a pH adjusting agent and the like, which are conventionally known in the art, can be appropriately blended in an appropriate amount according to the usage of the patch.

With regard to the medicinal component, there is no particular restriction as long as it is a chemical drug capable of percutaneous absorption. Examples include steroidal antiinflammatory agents such as prednisolone, dexamethasone, hydrocortisone, fluocinolone acetonide, betamethasone valerate, betamethasone dipropionate, clobetasone butyrate and prednisolone succinate; nonsteroidal antiinflammatory agents and the ester derivatives thereof such as methyl salicylate, glycol salicylate, indomethacin, ketoprofen, diclofenac, ibuprofen, flurbiprofen, felbinac, ketorolac, loxoprofen, suprofen, pranoprofen, tiaprofen, flufenamic acid, tenidap, aspirin, actarit, mizoribine, oxaprozin, mofezolac, etodolac, auranofin and indomethacin famesil; antiallergic drugs such as tranilast, azelastine, ketotifen, ibudilast, oxatomide, emedastin and epinastin; an antihistamine drug such as diphenhydramine, chlorpheniramine, promethazine and tripelennamine; drugs acting on the central nervous system such as chlorpromazine, nitrazepam, diazepam, phenobarbital and reserpine; hormone drugs such as insulin, testosterone, norethisterone, methyltestosterone, progesterone and estradiol; antihypertensive drugs such as clonidine, reserpine, guanethidine sulfate, efonidipine, alprenolol and nifedipine; cardiotonic drugs such as digitoxin and digoxin; antiarrhythmic drugs such as propranolol hydrochloride, procainamide hydrochloride, ajmaline, pindolol and tulobuterol hydrochloride; coronary vasodilators such as nitroglycerin, isosorbide nitrate, papaverine hydrochloride, nifedipine, diltiazem and nicorandil; local anesthetics such as lidocaine, procaine, procaine hydrochloride, benzocaine and tetracaine; painkillers such as morphine, aspirin, codeine, acetanilide and aminopyrine; muscle relaxants such as tizanidine, eperisone, tolperisone, inaperisone and dantrolene; antifungal drugs such as acetophenylamine, nitrofurazone, pentamycin, naphthiomate, miconazole, omoconazole, clotrimazole and butenafine hydrochloride; antimalignant tumor drugs such as 5-fluorouracil, busulfan, actinomycin, pleomycin and mitomycin; urinary incontinence drugs such as terolidine hydrochloride and oxybutynin hydrochloride; antiepileptic drugs such as nitrazepam and meprobamate; anti parkinson drugs such as chlorzoxazone, levodopa, amantadine, selegiline hydrochloride, ranolazine hydrochloride and ropinirole hydrochloride; antiemetic drugs such as granisetron, azasetron, ondansetron and ramosetron; drugs for the treatment of frequent urination such as oxybutynin, Ca antagonists such as nifedipine, psychotropic drugs such as fentanyl, morphine, imibramine; drugs for the treatment of vertigo such as difenidol and betahistine; cardiovascular drugs such as benzothiazepine; antitussive and expectorant drugs such as ketotifen, tulobuterol and tranilast; cerebral circulation improving drugs such as vinpocetine, nicergoline, nicorandil, clentiazem maleate, fasudil hydrochloride, benidipine hydrochloride and efonodipine hydrochloride; drugs for the treatment of cerebrovascular dementia such as docosahexaenoic acid, vinconate hydrochloride and nebracetam fumarate; drugs for the treatment of Alzheimer's disease such as donepezil hydrochloride, amiridine hydrochloride and memantine hydrochloride, polypeptide hormonal drugs such as lutenizing hormone-releasing hormone and thyrotropin releasing hormone; immunomodulators such as polysaccharides, auranofin and lobenzarit; choleretic drugs such as ursodeoxycholic acid; diuretic drugs such as hydroflumethiazide; diabetic drugs such as tolbutamide; drugs for the treatment of gout such as colchicines; antismoking coadjuvants such as nicotine, and furthermore, drugs such as vitamins, prostaglandins, stimulant drugs, hypnotic sedative drugs, autonomic nervous system drugs, peripheral vasodilating drugs and the like.

Examples of the skin-beautifying component include allantoin; glycyrrhizinic acid; dipotassium glycyrrhizinate; papain enzyme; L-arginine; arbutin; flavonoids; collagen; yogurt extracts; lecithin; ellagic acid; amino acids; kojic acid; proteins; saccharides; hormones; placenta extracts such as water-soluble placenta extract; silk or silk extract; components extracted from various herbal medicines such as aloe, gourd and liquorice; plant extracts such as *Angelica keiskei* extract, *Aspalathus Linearis* extract, *Leguminosae* extract, avocado extract, *Hydrangea macrophylla* extract, *Gynostemma pentaphyllum* extract, althea extract, arnica extract, almond extract, aloe extract, *Styrax benzoin* extract, *Rosa roxburghii* extract, *Polygonum cuspidatum* extract, *Ginkgo* extract, *Urtica dioica* extract, *Iris* root extract, oolong tea extract, fennel extract, turmeric extract, Rose Fruit extract, *Acanthopanax senticosus* extract, *Echinacea* leaf extract, *Pisum sativum* extract, *Scutellaria* root extract, *phellodendron* bark extract, *Coptis* extract, *Silybum marianum* extract, *Lagerstroemia speciosa* extract, barley extract, barley fermentation extract, *Hibiscus esculentus* extract, *Hypericum* extract, *Lamium album* extract, *ononis* extract, Watercress extract, orange extract, orange flower water, seaweed extract, persimmon tannin, *pueraria* root extract, *Valeriana* extract, cattail extract, *chamomilla* extract, *chamomilla* water, oat grass extract, *Chinese* quince extract, carrot extract, *Artemisia capillaris* extract, *glycyrrhiza* extract, raspberry extract, *ginkgo* nut extract, *Lagerstroemia speciosa* extract, *Sophora japonica* extract, buckwheat extract, Neroli extract, *magnolia* extract, *Sambucus nigra* extract, hibiscus extract, *Vaccinium macrocarpon* extract, *Japanese angelica* extract, guavafenone, *Sophorae Radix, Celosia argentea, Mucuna* extract, *Melothria* extract, lily bulb extract, raspberry extract, Lempuyang, green tea extract, applefenone, *Angelica acutiloba* extract, apricot extract, tea tree extract, peach extract, macadamia oil, almond oil, kiwi extract, *Cinchona succirubra* extract, cucumber extract, apricot kernel extract, quince seed extract, gardenia extract, *Sasa veitchii* extract, cumin extract, *Sophora flavescens* extract, walnut shell extract, grapefruit extract, *Clematis* extract, chlorella extract, mulberry extract, mulberry leaf extract, Millettia extract, cinnamon bark extract, *gentian* extract, *Geranium* extract, *Hovenia dulcis* extract, coffee extract, red tea extract, *Nuphar japonicum* extract, burdock extract, wheat germ extract, rice bran extract, rice bran fermentation extract, comfrey extract, *Asarum* extract, saffron extract, *Saponaria officinalis* extract, *Crataegus cuneata* extract, *Zanthoxylum piperitum* extract, *Lentinus edodes* extract, *Rehmannia glutinosa* extract, *Lithospermum erythrorhizon* extract, *Perilla frutescens* extract, linden extract, *Filipendula* extract, peony root extract, *Coix* extract, *Zingiber officinale* extract, *Acorus calamus* root extract, white birch extract, birch sap, *Lonicera japonica* extract, field horsetail extract, Stevia extract, sage extract, sage water, *Hedera helix* extract, *Crataegus oxycantha* extract, *Sambucus nigra* extract, *Juniperus communis* extract, *Achillea millefolium* extract, *Mentha piperita* extract, *Malva sylvestris* extract, celery extract, *Cnidium* extract, *Cnidium* water, *Swertia japonica* extract, soybean extract, *Zizyphi fructus* extract, thyme extract, tea extract, tea fruit extract, clove extract, *Polyporus umbellatus* extract, *Citrus unshiu* peel extract, *Camellia* extract, *Centella* extract, duke extract, *Terminalia sericea* extract, *Rubus suavissimus* extract, *Benincasae Semen* extract, *Angelica acutiloba* extract, *Calendula officinalis* extract, *Angelica acutiloba* water, *Cordyceps Sinensis* (Berkeley) Saccardo extract, peach kernel extract, *Picea jezoensis* extract, corn extract, *Houttuynia cordata* extract, tomato extract, *Potentilla tormentilla* extract, fermented soybean extract, carrot extract, garlic extract, *Rosa multiflora* extract, malt extract, malt root extract, *Ophiopogon japonicus* extract, parsley extract, distilled *Mentha* water, *Rosa rugosa* extract, *Hamamelis virginiana* extract, liquid extracted from *Hamamelis virginiana*, rose extract, parietalia extract, *Plectranthus japonicus* extract, cypress water, *Santalum album* extract, *Eriobotrya japonica* leaf extract, *Tussilago farfara* extract, *Poria cocos* extract, butcher's broom extract, grape extract, grape water, grape leaf extract, beech extract, prune extract, hayflower extract, gourd extract, gourd water, safflower extract, peony extract, hop extract, pine extract, *Arabian jasmine* extract, *Silybum marianum* extract, *Aesculus hippocastanum* extract, *Sapindus mukurossi* extract, *Swertia pseudochinensis* extract, *Murayakoengy* extract, *Melissa* extract, *Melilotus* extract, peach leaf extract, bean sprout extract, *Centaurea cyanus* extract, *Centaurea cyanus* water, *Eucalyptus globulus* extract, *Eucalyptus globulus* water, *Saxifraga stolonifera* extract, Yuzu extract, Lily extract, *Coix* extract, *Artemisia* extract, *Artemisia* water, Lavender extract, lavender water, blue-green algae extract, apple extract, apple water, *Litchi chinensis* extract, lettuce extract, lemon extract, *Astragalus sinicus* extract, rosemary extract, rosemary water, rose water, *Anthemis nobilis* extract, logwood extract, and burnet extract; vitamins such as vitamin A, vitamin C, vitamin D, vitamin E and other vitamins; vitamin C derivatives such as magnesium ascorbate phosphate, sodium ascorbate phosphate and ascorbate-2-glucoside, etc. In addition, chemical drugs having a skin whitening action such as diphenhydramine hydrochloride, diphenhydramine salicylate, diphenhydramine tannate, triprolidine hydrochloride, mequitazine, chlorpheniramine maleate, chlorpheniramine d-maleate, clemastine fumarate, promethazine hydrochloride, tranilast, sodium cromoglycate, ketotifen, arylsulfatase B, bufexamac, bendazac, butyl flufenamate, ibuprofen, indomethacin, aspirin, flurbiprofen, ketoprofen, piroxicam and 2-pyridinemethyl mefenamate, 5,6-dehydroarachidonic acid, 5,6-methano-$LTA_4$, esculetin, eupatilin, 4-demethyleupatilin, caffeinic acid and benoxaprofen are included and one or more kinds of these can be blended.

With regard to the moisturizing component, one or more kinds of an aqueous solution of succinylkefiran, an aqueous solution of acetylkefiran, an aqueous solution of maleylkefiran, malt root extract, *Rosae fructus* extract, orange extract, orange fruit juice, raspberry extract, kiwi extract, cucumber extract, gardenia jasminoides extract, grapefruit extract, *Crataegus cuneata* extract, *Zanthoxylum piperitum* extract, *Crataegus oxycantha* extract, *Juniperus communis* extract, *Zizyphi fructus* extract, *Ziziphus jujuba* extract, duke extract, tomato extract, grape extract, gourd extract, lime fruit juice, apple extract, apple fruit juice, lemon extract, lemon fruit juice and the like can be blended. Moreover, fruit extracts (fruit juices) also have an acting effect as a fragrance.

As the antioxidant, ascorbic acid, propyl gallate, butylhydroxyanisol, dibutylhydroxytoluene, nordihydroguaiaretic acid, tocopherol, tocopherol acetate and the like can be blended.

As the tackifier, casein, pullulan, agar, dextran, sodium alginate, soluble starch, carboxystarch, dextrin, carboxymethyl cellulose, sodium carboxymethyl cellulose, methylcellulose, ethylcellulose, hydroxyethyl-cellulose, polyvinyl alcohol, polyethylene oxide, polyacrylamide, polyacrylic acid, polyvinylpyrrolidone, carboxyvinyl polymer, polyvinyl ether, polymaleic acid copolymer, methoxyethylene maleicanhydride copolymer, isobutylene maleicanhydride copolymer, polyethylene imine and the like can be blended.

As the solubilizer, benzyl alcohol, pyrrothiodecane, peppermint oil, isopropyl myristate, crotamitone and the like can be blended.

As the pigment, the officially designated pigments such as Red No. 2 (amaranth), Red No. 3 (erythrosine), Red No. 102 (new coccine), Red No. 104-(1) (phloxine B), Red No. 105-(1) (rose bengale), Red No. 106 (acid red), Yellow No. 4 (tartrazine), Yellow No. 5 (sunset yellow FCF), Green No. 3 (fast green FCF), Blue No. 1 (brilliant blue FCF), Blue No. 2 (indigo carmine) and the like can be blended. As for the pigment, it is not particularly limited, however, it greatly affects the image of the preparation and leads to the improvement of feeling of use and activation feeling to the skin.

As the surfactant, an anionic surfactant such as sodium dioctyl sulfosuccinate, an alkylsulfate salt, a 2-ethylhexyl alkylsulfate ester sodium salt or sodium n-dodecyl benzenesulfonate; a cationic surfactant such as hexadecyl trimethylammonium chloride, octadecyl dimethyl benzyl ammonium chloride or polyoxyethylene dodecyl monomethylammonium chloride; and a nonionic surfactant such as polyoxyethylene stearylether, polyoxyethylene tridecylether, polyoxyethylene nonylphenylether, polyoxyethylene octylphenylether, polyoxyethylene monostearate, sorbitan monostearate, sorbitan monopalminate, sorbitan sesquioleate, polyoxyethylene sorbitan monolaurate, polyoxyethylene sorbitan monooleate, glycerol monostearate, polyglycerin fatty acid ester or polyoxyethylene octadecyl amine can be blended.

As the UV absorber, p-aminobenzoic acid, p-aminobenzoate ester, amyl p-dimethylaminobenzoate, salicylate ester, menthyl anthranilate, umbelliferone, esculin, benzyl cinnamate, cinoxate, guaiazulene, urocanic acid, 2-(2-hydroxy-5-methylphenyl) benzotriazole, 4-methoxybenzophenone, 2-hydroxy-4-methoxy benzophenone, dioxybenzone, octabenzone, dihydroxy dimethoxybenzophenone, slisobenzone, benzoresorcinol, octyl dimethyl p-aminobenzoate, ethylhexyl p-methoxycinnamate and the like can be blended.

As the inorganic filler, titanium oxide, talc, zinc oxide, silicate hydrate, magnesium carbonate, calcium hydrogen phosphate, magnesium silicate, diatomaceous earth, anhydrous silicic acid, bentonite and the like can be blended.

As the pH adjusting agent, acetic acid, formic acid, lactic acid, tartaric acid, oxalic acid, benzoic acid, glycolic acid, malic acid, succinic acid, hydrochloric acid, nitric acid, sulfuric acid, sodium hydroxide, potassium hydroxide, methylamine, ethylamine, propylamine, dimethylamine, diethylamine, dipropylamine, trimethylamine, triethylamine, tripropylamine, monomethanolamine, monoethanolamine, monopropanolamine, dimethanolamine, diethanolamine, diprpanolamine, trimethanolamine, triethanolamine, tripropanolamine and the like can be blended.

It is desired to consider that the pH value of the paste appropriately blended with each of the above-mentioned components in a suitable amount not to give irritation to the skin. The pH of the paste is preferably in the range of 4 to 8, more preferably in the range of 5 to 7.

As the method of producing the sheet-type patch of the present invention, the above-mentioned components are uniformly mixed and/or dissolved while stirring, and spread on the non-dyed or dyed above-mentioned support. Then, a release film is attached on it, and it is cut in a predetermined shape as needed or formed into a roll shape, thereby the patch is produced. Further, a sheet-type patch is desirably stored in a sealed bag or container until use in order to prevent contamination during storage, a decrease in the effect by the evaporation or the like of the volatile substance, etc.

With regard to thus obtained sheet-type patch of the present invention, the maximum strength of the tensile strength of the patch itself is desirably 20 to 150 N/50 mm, and the maximum load of the tear strength is desirably 1 to 15 N.

The sheet-type patch of the present invention composed of the above configuration is safe for the skin, imparts a good feeling of use and shows an excellent acting effect as well as a cooling effect on the affected part. Furthermore, the patch can be used by easily cutting it by hand into a necessary size in the state of the preparation provided with a release film attached thereto and the remaining part after tearing can be stably used or stored.

The sheet-type patch of the present invention is especially effective when it is used as, for example, a patch for compress, etc.

Incidentally, all the content described in the specification of Japanese Patent Application No. 2002-091297 is incorporated into this description.

EXAMPLES

Hereunder, the present invention is explained further in detail by reference to Examples and Test Examples, but the present invention is not limited by these Examples and Test Examples.

Example 1

Purified water (58.25 wt %), synthetic aluminum silicate (1 wt %), titanium oxide (1 wt %), gelatin (2.5 wt %), methylparaben (0.1 wt %), propylparaben (0.05 wt %), polyvinyl alcohol (2.5 wt %), glycerin (25 wt %), polyglycerol polyglycidyl ether (0.05 wt %), polyacrylic acid (3 wt %), a partial neutralization product of polyacrylic acid (3 wt %), glycol salicylate (1.25 wt %), l-menthol (1 wt %), tocopherol acetate (1 wt %) and dl-camphor (0.3 wt %) were stirred until they were dispersed and dissolved uniformly. The mixture was then spread on the following support so that the ratio became 1000 g/m$^2$, and the following release film was attached thereto. Thereafter, it was cut into a 5 cm×30 cm piece, thus the sheet-type patch 1 was obtained.

Support
(composition) polyester
(fiber length) 38 mm
(tensile strength) 13 N/50 mm
(elongation at maximum load) 15%
(weight per unit area) 80 g/m$^2$
Release Film
(composition) ethylene vinyl acetate copolymer
(hole diameter) 70 μm
(distance between centers of holes in a longitudinal direction) 1000 μm
(distance between centers of holes in a lateral direction) 1000 μm
(tensile strength) 25 N/50 mm
(thickness) 76 μm

Example 2

The sheet-type patch 2 was produced in the same manner as in Example 1 except that the support and the release film were changed to the following ones.

Support
(composition) rayon+pulp (1:1)
(fiber length) rayon 50 mm+pulp 1.5 mm
(tensile strength) 31 N/50 mm
(elongation at maximum load) 77%
(weight per unit area) 80 g/m$^2$
Release Film
(composition) ethylene vinyl acetate copolymer
(hole diameter) 145 μm
(distance between centers of holes in a longitudinal direction) 1000 μm
(distance between centers of holes in a lateral direction) 1000 μm
(tensile strength) 33 N/50 mm
(thickness) 102 μm

Example 3

Purified water (79.02 wt %), gelatin (0.5 wt %), methylparaben (0.2 wt %), propylparaben (0.05 wt %), propylene glycol (5 wt %), glycerin (5 wt %), ethylene glycol diglycidyl ether (0.02 wt %), a partial neutralization product of polyacrylic acid (5 wt %), dipotassium glycyrrhizinate (0.1 wt %), tocopherol acetate (0.1 wt %), aluminum acetate (0.01 wt %) and synthetic aluminum silicate (5 wt %) were stirred until they were dispersed and dissolved uniformly. The mixture was then spread on the following support so that the ratio became 714 g/m$^2$, and the following release film was attached thereto. Thereafter, it was cut into a 5 cm×30 cm piece, thus the sheet-type patch 3 was obtained.

Support
(composition) polyester
(fiber length) 38 mm
(tensile strength) 13 N/50 mm
(elongation at maximum load) 15%
(weight per unit area) 80 g/m$^2$
Release Film
(composition) polyethylene
(hole diameter) 10 μm
(distance between centers of holes in a longitudinal direction) 100 μm
(distance between centers of holes in a lateral direction) 1000 μm
(tensile strength) 24 N/50 mm
(thickness) 76 μm

Example 4

Purified water (34.8 wt %), glycerin (30 wt %), methylparaben (0.1 wt %), kaolin (1 wt %), gelatin (2 wt %), sorbitan polyglycidyl ether (0.05 wt %), polyacrylic acid (4 wt %), a partial neutralization product of polyacrylic acid (3.5 wt %), synthetic aluminum silicate (0.5 wt %), polyvinyl pyrrolidone (3 wt %), polyethylene glycol (15 wt %), propylene glycol (5 wt %), ketoprofen (0.3 wt %), 1-menthol (0.3 wt %), crotamiton (0.25%) and oxybenzone (0.2 wt %) were stirred until they were dispersed and dissolved uniformly. The mixture was then spread on the following support so that the ratio became 500 g/m$^2$, and the following release film was attached thereto. Thereafter, it was cut into a 5 cm×30 cm piece, thus the sheet-type patch 4 was obtained.

Support
(composition) polyester
(fiber length) 38 mm
(tensile strength) 13 N/50 mm
(elongation at maximum load) 15%
(weight per unit area) 80 g/m$^2$
Release Film
(composition) polypropylene
(hole diameter) 70 μm
(distance between centers of holes in a longitudinal direction) 1000 μm
(distance between centers of holes in a lateral direction) 2000 μm
(tensile strength) 11 N/50 mm
(thickness) 24 μm

Example 5

The sheet-type patch 5 was produced in the same manner as in Example 4 except that the support and the release film were changed to the following ones.

Support
(composition) polyester
(fiber length) 38 mm
(tensile strength) 13 N/50 mm
(elongation at maximum load) 15%
(weight per unit area) 80 g/m$^2$
Release Film
(composition) ethylene vinyl acetate copolymer
(hole diameter) 70 μm
(distance between centers of holes in a longitudinal direction) 1000 μm
(distance between centers of holes in a lateral direction) 1000 μm
(tensile strength) 48 N/50 mm
(thickness) 150 μm

Example 6

The sheet-type patch 6 was produced in the same manner as in Example 4 except that the support and the release film were changed to the following ones.

Support
(composition) polyester
(fiber length) 38 mm
(tensile strength) 46 N/50 mm
(elongation at maximum load) 95%
(weight per unit area) 200 g/m$^2$
Release Film
(composition) polyethylene terephthalate/ethylene vinyl acetate copolymer
(hole diameter) 70 μm
(distance between centers of holes in a longitudinal direction) 500 μm
(distance between centers of holes in a lateral direction) 1000 μm
(tensile strength) 97 N/50 mm
(thickness) 30 μm

Example 7

The sheet-type patch 7 was produced in the same manner as in Example 4 except that the support and the release film were changed to the following ones.

Support
(composition) polyester
(fiber length) 76 mm (tensile strength) 3 N/50 mm
(elongation at maximum load) 3%
(weight per unit area) 20 g/m$^2$
Release Film
(composition) ethylene vinyl acetate copolymer
(hole diameter) 1200 μm
(distance between centers of holes in a longitudinal direction) 2000 μm
(distance between centers of holes in a lateral direction) 2000 μm
(tensile strength) 21 N/50 mm
(thickness) 150 μm Comparative Example 1

The sheet-type patch C was produced in the same manner as in Example 1 except that the support and the release film were changed to the following ones.
Support
(composition) polyester
(fiber length) 50 mm
(tensile strength) 15 N/50 mm
(elongation at maximum load) 214%
(weight per unit area) 100 g/m$^2$
Release Film
(composition) polyethylene terephthalate
(hole diameter) 0 μm
(distance between centers of holes in a longitudinal direction) 0 μm
(distance between centers of holes in a lateral direction) 0 μm
(tensile strength) 143 N/50 mm
(thickness) 16 μm Test Example 1

Tensile Strength Test

A tensile strength test was carried out for the sheet-type patches 1, 2, 3, 4, 5, 6, 7 and C. The test was carried out, as a rule, in accordance with the method described in JIS L1912 "tensile strength and elongation rate" in "Iryouyou Fusyokufu Shiken Houhou (Test method for unwoven fabrics for medical use)", and the measurements were carried out under the conditions that the sample width was 50 mm, the distance between clamps was 50 mm and the tensile speed was 300 mm/min.

In the test, measurements were carried out 5 times for each sample, and the mean value was calculated. Table 1 shows the test results.

TABLE 1

| Sample | Maximum strength of tensile strength (N/50 mm) |
| --- | --- |
| Sheet-type patch 1 | 45 |
| Sheet-type patch 2 | 69 |
| Sheet-type patch 3 | 41 |
| Sheet-type patch 4 | 29 |
| Sheet-type patch 5 | 71 |
| Sheet-type patch 6 | 147 |
| Sheet-type patch 7 | 23 |
| Sheet-type patch C | 172 |

Test Example 2

Tear Strength Test

A tear strength test was carried out for the sheet-type patches 1, 2, 3, 4, 5, 6, 7 and C. The test was carried out, as a rule, in accordance with the Trapezoid method described in JIS L1912 "tear strength" in "Iryouyou Fusyokufu Shiken Houhou (Test method for unwoven fabrics for medical use)", and the measurements were carried out under the conditions that the sample width was 50 mm, the distance between clamps was 100 mm and the tensile speed was 100 mm/min.

In the test, measurements were carried out 5 times for each sample, and the mean value was calculated. Table 2 shows the test results.

TABLE 2

| Sample | Maximum load of tear strength (N) |
| --- | --- |
| Sheet-type patch 1 | 7 |
| Sheet-type patch 2 | 9 |
| Sheet-type patch 3 | 5 |
| Sheet-type patch 4 | 3 |
| Sheet-type patch 5 | 10 |
| Sheet-type patch 6 | 15 |
| Sheet-type patch 7 | 1 |
| Sheet-type patch C | 19 |

Test Example 3

Sensory Evaluation

A sensory evaluation was carried out for the sheet-type patches 1, 2, 3, 4, 5, 6, 7 and C by giving 10 healthy subjects for each sample. An absolute evaluation was carried out by handing one sheet of the sample (with a release film) to the subjects, and allowing them to tear it into a size at choice and to apply it to the shoulder for 6 hours. Thereafter, the subjects were allowed to make an evaluation in terms of "hand-tearable property", "external appearance of cut surface" and "feeling of use". Table 3 shows the test results of "hand-tearable property", Table 4 shows the test results of "external appearance of cut surface" and Table 5 shows the test results of "feeling of use".

TABLE 3

| Sample | Bad | Good |
| --- | --- | --- |
| Sheet-type patch 1 | 0 | 10 |
| Sheet-type patch 2 | 1 | 9 |
| Sheet-type patch 3 | 0 | 10 |
| Sheet-type patch 4 | 0 | 10 |
| Sheet-type patch 5 | 1 | 9 |
| Sheet-type patch 6 | 3 | 7 |
| Sheet-type patch 7 | 0 | 10 |
| Sheet-type patch C | 10 | 0 |

TABLE 4

| Sample | Bad | Good |
| --- | --- | --- |
| Sheet-type patch 1 | 0 | 10 |
| Sheet-type patch 2 | 1 | 9 |
| Sheet-type patch 3 | 0 | 10 |
| Sheet-type patch 4 | 1 | 9 |
| Sheet-type patch 5 | 1 | 9 |
| Sheet-type patch 6 | 2 | 8 |

TABLE 4-continued

| Sample | Bad | Good |
| --- | --- | --- |
| Sheet-type patch 7 | 4 | 6 |
| Sheet-type patch C | 10 | 0 |

TABLE 5

| Sample | Bad | Good |
| --- | --- | --- |
| Sheet-type patch 1 | 0 | 10 |
| Sheet-type patch 2 | 0 | 10 |
| Sheet-type patch 3 | 0 | 10 |
| Sheet-type patch 4 | 0 | 10 |
| Sheet-type patch 5 | 0 | 10 |
| Sheet-type patch 6 | 0 | 10 |
| Sheet-type patch 7 | 0 | 10 |
| Sheet-type patch C | 4 | 6 |

Test Example 4

Skin Safety Test

A 48-hour closed patch test was carried out for the sheet-type patches 1, 3, 4 and C. In the test, 30 healthy men and women were provided with the respective samples and applied them to the inner part of the upper arm, and the skin irritation 1 hour and 24 hours after the detachment was evaluated. The test results are shown in Table 6.

TABLE 6

| | | Evaluation | | | | | |
| --- | --- | --- | --- | --- | --- | --- | --- |
| | Sample | ++ | + | ± | − | Total (Number of people) | Positive percentage (%) ±or more |
| 1 hour after detachment | patch 1 | 0 | 0 | 1 | 29 | 30 | 3.3 |
| | patch 3 | 0 | 0 | 0 | 30 | 30 | 0.0 |
| | patch 4 | 0 | 0 | 1 | 29 | 30 | 3.3 |
| | patch C | 0 | 0 | 1 | 29 | 30 | 3.3 |
| 24 hours after detachment | patch 1 | 0 | 0 | 0 | 30 | 30 | 0.0 |
| | patch 3 | 0 | 0 | 0 | 30 | 30 | 0.0 |
| | patch 4 | 0 | 0 | 0 | 30 | 30 | 0.0 |
| | patch C | 0 | 0 | 0 | 30 | 30 | 0.0 |

From the results of the above-mentioned sensory evaluation, it was found that the sheet-type patch of the present invention is safe for the skin, imparts a good feeling of use, shows an excellent acting effect as well as a cooling effect on the affected part, and furthermore, it can be used by easily tearing it by hand into a necessary size in the state of the preparation provided with a release film attached thereto and the remaining part after tearing can be stably used or stored.

INDUSTRIAL APPLICABILITY

The sheet-type patch of the present invention is safe for the skin, imparts a good feeling of use and shows an excellent acting effect as well as a cooling effect on the affected part. Furthermore, the patch can be used by easily tearing it by hand into a necessary size in the state of the preparation provided with a release film attached thereto and the remaining part after tearing can be stably used or stored. Therefore, it is also excellent from hygienical and economical viewpoints. In addition, since it is safe for the skin, it can be used for treatment of an injured part, skin adjustment, beauty and the like, and it can be applied in the fields of medicinal and quasi-drug preparations and cosmetic products, therefore, it is industrially very useful.

The invention claimed is:

1. A sheet-type patch, comprising a non-woven fabric support, a paste applied onto the support and a release film, having been punched with holes, wherein the punched holes are made only in release film, attached thereto, covering the paste,
    wherein the support consisting of a non-woven fabric is made from a yarn of 1 to 80 mm in fiber length, and the release film has holes thereon of 10 to 1200 μm in diameter and a maximum tensile strength of 10 to 100 N/50 mm in order to provide a simultaneous tear of the release film, the support, and the paste, as well as to provide stable directional tearing at any position to achieve a desired size of patch sheet; and
    wherein the holes of the release film are aligned to adjoin each other in both longitudinal and lateral rows over the film.

2. The sheet-type patch according to claim 1, wherein the distance between the centers of the longitudinally and laterally adjoining holes is 100 to 2000 μm.

3. The sheet-type patch according to claim 1, wherein the thickness of the release film is 20 to 150 μm.

4. The sheet-type patch according to claim 1, wherein the release film is a film formed by combining one or more materials selected from the group of polyethylene, polypropylene, polyethylene terephthalate, an ethylene vinyl acetate copolymer, an ethylene vinyl alcohol copolymer, polyvinyl chloride, polyurethane, polyester and polyamide.

5. The sheet-type patch according to claim 1, wherein the maximum strength of the tensile strength of the support is 3 to 50 N/50 mm.

6. The sheet-type patch according to claim 1, wherein the elongation at maximum load of the support relative to the initial length is 3 to 100%.

7. The sheet-type patch according to claim 1, wherein the weight per unit area of the support is 20 to 200 g/m$^2$.

8. The sheet-type patch according to claim 1, wherein the support is a nonwoven fabric made by entangling, heat fusion bonding, pressure bonding or binder bonding in combination with one or more materials selected from selected from the group of polyethylene, polypropylene, polyethylene terephthalate, an ethylene vinyl acetate copolymer, polyvinyl chloride, polyurethane, polyester, polyamide, rayon, pulp and cotton.

9. The sheet-type patch according to claim 1, wherein the maximum strength of the tensile strength of the sheet-type patch is 20 to 150 N/50 mm.

10. The sheet-type patch according to claim 1, wherein the maximum load of the tear strength of the sheet-type patch is 1 to 15 N.

11. The sheet-type patch according to claim 1, wherein the sheet-type patch is a patch for compress.

12. The sheet-type patch according to claim 1, wherein the sheet-type patch further comprises one or more medicinal agents.

13. The sheet-type patch according to claim 1, wherein the sheet-type patch further comprises one or more cosmetic agents.

* * * * *